United States Patent [19]

Knifton

[11] 4,268,689

[45] May 19, 1981

[54] MANUFACTURE OF VICINAL GLYCOL ESTERS FROM SYNTHESIS GAS

[75] Inventor: John F. Knifton, Austin, Tex.

[73] Assignee: Texaco Development Corp., White Plains, N.Y.

[21] Appl. No.: 103,763

[22] Filed: Dec. 14, 1979

Related U.S. Application Data

[63] Continuation-in-part of Ser. No. 968,655, Dec. 11, 1978, abandoned.

[51] Int. Cl.³ ............... C07C 27/06; C07C 69/14; C07C 69/16
[52] U.S. Cl. ................ 560/263; 260/410.6; 260/410.9 R; 260/449 R; 260/449 L; 560/265; 560/227; 252/428; 252/429 R; 252/429 A; 252/429 B; 252/431 R; 252/431 P; 252/431 N; 252/437; 252/438; 252/441; 252/472; 252/473; 252/474
[58] Field of Search ............... 560/263, 178, 190, 198, 560/226, 227, 230, 231, 265; 260/410.6, 410.9 R, 410.9 C, 449 R, 449 L, 449.5

[56] References Cited

U.S. PATENT DOCUMENTS

| 2,534,018 | 12/1950 | Gresham et al. | 560/263 |
| 2,549,470 | 4/1951 | Howk et al. | 568/902 |
| 2,632,014 | 3/1953 | Gresham | 260/449 R |
| 3,040,090 | 6/1962 | Alderson | 568/902 |
| 3,767,709 | 10/1973 | Fenton | 568/902 |
| 3,878,290 | 4/1975 | Walker et al. | 423/417 X |
| 3,944,588 | 3/1976 | Kaplan | 260/449 L |
| 4,013,700 | 3/1977 | Cawse | 260/449 R |
| 4,098,727 | 7/1978 | Haag et al. | 260/449 R |
| 4,170,605 | 10/1979 | Williamson et al. | 260/449 L |

FOREIGN PATENT DOCUMENTS

| 2644185 | 4/1977 | Fed. Rep. of Germany | 260/449 R |
| 1501892 | 2/1978 | United Kingdom | 260/449 R |

OTHER PUBLICATIONS

Pichler et al., Brennstoff Chemie, No. 9, Bd. 48, 1967, pp. 226–272.

*Primary Examiner*—Howard T. Mars
*Attorney, Agent, or Firm*—Carl G. Ries; Robert A. Kulason; James L. Bailey

[57] ABSTRACT

This invention concerns the improved preparation of glycol esters, such as ethylene glycol diesters, by reaction of carbon monoxide and hydrogen in the presence of a ruthenium or osmium-containing catalyst and a liquid phase medium containing a carboxylic acid co-reactant. The improvement which comprises the invention here also involves use of a co-catalyst species selected from the group consisting of one or more alkali metal salts, alkaline earth metal salts, quaternary ammonium salts, iminium salts and quaternary aliphatic phosphonium salts.

24 Claims, No Drawings

MANUFACTURE OF VICINAL GLYCOL ESTERS FROM SYNTHESIS GAS

REFERENCE TO RELATED APPLICATION

This application is a continuation-in-part application of copending application Ser. No. 968,655 filed Dec. 11, 1978 now abandoned.

SUMMARY AND BACKGROUND OF INVENTION

This invention concerns an improved process for preparing vicinal glycol ester compounds, including ester derviatives of ethylene glycol, by reaction of oxides of carbon with hydrogen.

In copending, commonly assigned application Ser. No. 103,765, filed Dec. 14, 1979, the inventive process concerns the synthesis of glycol esters, particularly the ester derivative of ethylene glycol, by the catalytic reaction of carbon monoxide and hydrogen in the presence of a liquid medium containing a carboxylic acid co-reactant such as acetic acid. Catalysis is effected in the presence of a catalyst containing osmium or ruthenium transition metals, with the latter being most preferred. The process is exemplified by, but not limited to, the one step synthesis of ethylene glycol diacetate, from carbon monoxide, hydrogen mixtures — commonly known as synthesis gas — in the presence of an acetic acid (HOAc) liquid medium according to the stoichiometry of eq I below:

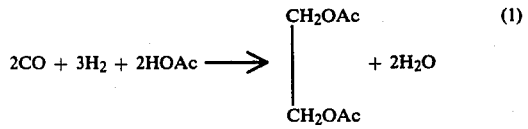

Other valuable products include methyl acetate and ethyl acetate as follows:

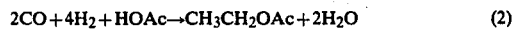

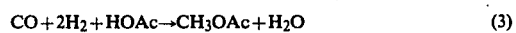

Methyl and ethyl acetates are used widely as solvents, primarily for surface coatings.

While use of synthesis gas is known as a building block in making a variety of chemicals there is no simple, direct, yet economical route toward production of glycol ester using relatively inexpensive catalysts. Catalysts used in making the glycol esters or free glycol material directly have proven to be very costly and/or in short supply. Glycol esters such as glycol acetate may be easily hydrolyzed to the free glycol as set out in Belgium Pat. No. 749,685 and other publications. Ethylene glycol is a particularly important component in making polyester fiber and in formulating antifreeze compositions.

Thus, in recent years, a large number of patents have been isused dealing with the synthesis of lower molcular weight hydrocarbons, olefins, alkanols etc. from synthesis gas. Of particular note U.S. Pat. No. 2,636,046, discloses the synthesis of polydydric alcohols and their derivatives by reaction between carbon monoxide and hydrogen at elevated pressures (>1500 atm or 22,000 psi) and temperatures to 400° C. using certain cobalt-containing catalysts. More recently, in Belguim Pat. No. 793,086 and U.S. Pat. No. 3,940,432 there is described the cosynthesis of methanol and ethylene glycol from mixtures of carbon monoxide and hydrogen using a rhodium complex catalyst. Typically, CO-hydrogenation is effected at 8000 psi of 1:1 $H_2/CO$ synthesis gas, at 220° C., using tetraglyme as the solvent, and dicarbonylacetylacetonatorhodium(I) in combination with an organic Lewis base as the catalyst precursor. (For summary of the work, see: R. L. Pruett, Annals New York Academy of Sciences, Vol. 295 p. 239 (1977)). While other metals of Group VIII of the Periodic Table have been tested for activity under similar conditions, including cobalt, ruthenium, copper, manganese, iridium and platinum, only cobalt was found to have slight activity. The use of ruthenium compounds in particular failed to produce polyfunctional products such as ethylene glycol. This is illustrated in U.S. Pat. No. 3,833,634 for solutions of trirutheium dodecacarbonyl.

PROCESS EMBODIMENTS

The present invention constitutes a still further improvement of my companion case which in its broadest aspects involves preparation of vicinal glycol esters from mixtures of carbon monoxide and hydrogen (synthesis gas) by contacting said synthesis gas with an aliphatic carboxylic acid in presence of a catalyst containing a ruthenium or osmium transition metal or mixtures thereof and heating said reaction mixture under superatomospheric pressures until the desired esters are formed.

In the narrower and more preferred practice of that invention, ethylene glycol type esters are prepared from a synthesis gas mixture of carbon monoxide and hydrogen by a process comprising the following steps:

(a) Contacting said mixture of carbon monoxide and hydrogen with a liquid medium containing one or more aliphatic carboxylic acids and a ruthenium-containing catalyst.

(b) Heating said reaction mixture to a temperature of between about 100° C. and 350° C., at superatomospheric pressures of 500 psi or greater with sufficient carbon monoxide and hydrogen to satisfy the stoichiometry of the desired ester synthesis, until substantial formation of the desired ester of ethylene glycol has been achieved.

The ethylene glycol ester is preferably then isolated by conventional means.

The improvement here involves use as a co-catalyst one or more species selected from the group consisting of alkali metal salts, alkaline earth metal salts, quaternary ammonium salts, iminium salts and quaternary phosphonium salts.

In order to present the inventive concept in the greatest possible detail as to promote its understanding, the following supplementary disclosure is submitted. The basic invention, improved upon here is practiced as follows. A. Catalyst Composition — Catalysts that are suitable in the practice of this invention contain osmium or ruthenium transition metals or mixtures of these metals. The ruthenium or osmium-containing catalyst may be chosen from a wide variety of organic inorganic compounds, complexes, etc., as will be shown and illustrated below. It is only necessary that the catalyst precursor actually employed contain said transition metal in any of its ionic states. The actual catalytically active species are then believed to comprise ruthenium or osmium in complx combination with carbon monoxide and hydrogen. The most effective catalysis is achieved where the ruthenium or osmium hydrocarbonyl species are solubilized in the carboxylic acid co-reactant employed to satisfy the stoichiometry of eq 1-3.

While the invention will be more specifically discussed below in terms of typical ruthenium-containing forms or species it is understood that osmium may be employed in like forms in most cases without departing from the scope of the invention.

The preferred ruthenium catalyst precursors may take many different forms. For instance, the ruthenium may be added to the reaction mixture in an oxide form, as in the case of, for example, ruthenium(IV) oxide, hydrate, anhydrous rutheium(IV) dioxide and ruthenium(VIII) tetraoxide. Alternatively, it may be added as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid (see Section B, below), for example, ruthenium(III) acetate, ruthenium(III) propionate, ruthenium butyrate, ruthenium(III) trifluoroacetate, ruthenium octanoate, ruthenium napththenate, ruthenium valerate and ruthenium(III) acetylcacetone. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4 Ru_4(CO)_{12}$, and substituted carbonyl species such as the tricarbonylruthenium(II) chloride dimer, $[Ru(CO)_3Cl_2]_2$.

In a preferred embodiment of the invention ruthenium is added to the reaction zone as one or more oxide, salt or carbonyl derivative species in combination with one or more Group VB tertiary donor ligands. The key elements of the Group VB ligands include nitrogen, phosphorous, arsenic and antimony. These elements, in their trivalent oxidation states, particularly tertiary phosphorous and nitrogen, may be bonded to one or more alkyl, cycloalkyl, aryl, substituted aryl, aryloxide, alkoxide and mixed alkaryl radicals, each containing from 1 to 12 carbon atoms, or they may be part of a heterocyclic ring system, or be mixtures thereof. Illustrative examples of suitable ligands that may be used in this invention include: triphenylphosphine, tri-n-butylphosphine, triphenylphosphite, triethylphosphite, trimethylphoshite, trimethylphoshine, tri-p-methoxyphenylphoshine, triethylphosphine, trimethylarsine, triphenylarsine, tri-p-tolylphosphine, tricyclohexylphosphine, dimethylphenylphosphine, trioctylphosphine, tri-o-tolylphosphine, 1,2-bis(diphenylphosphino)ethane, triphenylstibine, trimethylamine, tripropylamine, tri-n-octylamine, pyridine, 2,2'-dipyridyl, 1,10-phenanthroline, quinoline, N,N'dimethylpiperazine, 1,8l-bis(dimethylamino)napththalene and N,N-dimethylaniline.

One or more of theses ruthenium-tertiary Group VB donor ligand combinations may be preformed, prior to addition to the reaction zone, as in the case, for example, of tris(triphenylphosphine)ruthenium(II) chloride and tricarbonylbis(triphenylphosphine)ruthenium or alernatively, said complexes may be formed in situ.

The performances of each of these classes of ruthenium catalyst precursors are illustrated by the accompanying examples, described below.

Similar catalyst combinations, containing osmium rather than ruthenium as the transition-metal component, are also suitable for the desired synthesis of alkanol and polyhydric alcohol ester from synthesis gas. B. Carboxylic Acids — Carboxyl acids useful in the process of this invention form the acid moiety of the desired methyl, ethyl and glycol esters products. Preferably, said acids are also useful as solvents for the transition-metal catalysts, particularly the ruthenium catalyst combinations. Suitable carboxylic acids includes aliphatic acids, alicyclic monocarboxylic acids, heretocyclic acids and aromatic acids, both substituted and non-substituted. For example, this invention contemplates the use of lower mono aliphatic acids of 1 to 12 carbon atoms such as formic acid, acetic, proponic, butyric, isobutyric, valeric, caproic, capric, perlargonic and lauric aids, together with dialiphatic acids of 2 or 6 carbons, such as oxalic, malonic, succinic and adipic acids. The invention further contemplates the use of substituted monoaliphatic acids containing one or more functional substituents, such as the lower alkoxy, chloro, fluoro, cyano, alkylthio, and amino functional groups, examples of which include acetoacetic acid, dichloroacetic and trifluoroacetic acid, chloropropionic acid, trichloroacetic acid, monofluoroacetic acid and the like. Among the suitable aromatic acids contemplated are benzoic acid, naphthoic acids, toluic acids, chlorobenzoic acids, aminobenzoic acids and phenylacetic acid. The alicyclic monocarboxylic acids may contain from 3 to 6 carbons in the ring, both substituted and unsubstituted, and may contain one or moe carboxyl groups, such as cyclopentanecarboxylic acid and hexahydrobenoic acids. The heterocyclic acids may contain 1 to 3 fused rings both substituted and unsubstituted together with one or more carboxylic groups, examples incllude quinolinic, furoic and picolinic acids. Mixtures of said classes of carboxylic acids, in any ratio, may also be used in the inventive process. The preferred carboxylic acids are the lower aliphatic acids such as acetic acid, propionic acid and butyric acid, together with substituted aliphatic acids such as trifluoroacetic acid. C. Catalyst Concentration — The quantity of ruthenium catalyst employed in the instant invention is not critical and may vary over a wide range. In general, the novel process is desirably conducted in the presence of a catalytically effective quantity of the active ruthenium species which gives the desired ester products in reasonable yields. Reaction proceeds when employing as little as about $1 \times 10^{-6}$ weight percent, and even lesser amounts, of ruthenium, basis the total weight of the reaction mixture. The upper concentration is dictated by a variety of factors including catalyst cost, partial pressures of carbon monoxide and hydrogen, operating temperature and choice of carboxylic acid diluent/reactant. A ruthenium catalyst concentration of from about $1 \times 10^{-5}$ to about 10 weight percent ruthenium, based on the total weight of reaction mixture, is generally desirable in the practice of this invention. Similar concentration ranges are employed in the case of osmium. D. Operating Temperature — The temperature range which can usefully be employed in these ester syntheses is a variable dependent upon other experimental factors, including the choice of carboxylic acid co-reactant, the pressure, and the concentration and particular choice of catalyst among other things. Again using ruthenium as the active metal, the range of operability is from about 100° to 350° C. when superatomspheric pressures of syngas are employed. A narrower range of 150°-260° C. represents the preferred temperature range when the major products are methyl, ethyl and glycol acetates. Table I is evidency of how the narrower range is derived. E. Pressure — Superatmospheric pressures of 500 psi or greater lead to substantial yield of desirable alkanol and vicinal glycol ester by the process of this invention. A preferred operating range for solutions of ruthenium(III) acetylacetonate in acetic acid is from 1000 psi to 7500 psi, although pressures above 7500 psi also provide useful yields of desired ester. Table I is evidency of this preferred, narrower range of operating pressures. The pressures referred to here represent the total pressure generated by all the reactants, although they are substantially due to the carbon monoxide and hydrogen fractions in these examples. F. Gas Composition — The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions such as carbon dioxide, hydrocarbons such as methane, ethane, propane and the like, ethers such as dimethyl ether, methylethyl ether and diethyl ether, alkanols such as methanol and acid esters such as methyl acetate.

In all syntheses, the amount of carbon monoxide and hydrogen present in the reaction mixture should be sufficient to satisfy the stoichiometry of eq (1)→(3). G. Product Distribution — As far as can be determined, without limiting the invention thereby, the ruthenium-catalyst one-step CO-hydrogenation process disclosed herein leads to the formation of three classes of primary products, namely the methanol, ethanol and ethylene glycol ester derivatives of the corresponding co-reactant carboxylic acid, which products may be easily separated from one another. In the case then where acetic acid is the coreactant, the principal products are methyl acetate, ethyl acetate and the valuable ethylene glycol diacetate product which may be easly isolated from the first two by-products. Minor by-products detected in the liquid product fraction include small amounts of water, glycol monoacetate, propyl acetate and dimethyl ether. Carbon dioxide, methane and dimethyl either may be detected in the off-gas together with unreacted carbon monoxide and hydrogen. H. Mode of Operation — The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ester product, and said material may be recovered by methods well known in the art, such as distillation, fractionation, extraction and the like. A fraction rich in ruthenium catalyst components may then be recycled to the reaction zone, if desired, and additional ester products generated by CO hydrogenation. I. Identification Procedures — The products of CO-hydrogenation have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts by weight, all temperatures are in degrees centigrade and all pressures in pounds per square inch guage (psi).

COCATALYST COMPOSITIONS

The improvement here to use of osmium or ruthenium catalyst precursors, useful in the conversion of carbon monoxide-hydrogen mixtures to methanol, ethanol, and glycol ester derivatives, consists of one or more suitable ruthenium or osmium oxide, salt and/or carbonyl or other derivative species in combination with a co-catalyst. There are several classes of suitable co-catalysts. One such class which may be added to the reaction mixtures to enhance the activity of the solubilized ruthenium or osmium catalysts are the salts of the alkali and alkaline earth metals. Illustrative examples of effective alkali metal salts include the alkali metal halides, for instance, the fluoride, chloride, bromide and iodide salts, together with the alkali and alkaline earth metal salts of suitable carboxylic acids. The preferred alkali and alkaline earth metal carboxylates are the acetate, propionate and butyrate salts of sodium, potassium, barium and cesium. These salts may be added over a wide range of concentrations, from about 0.01 to about at least $10^2$ moles of alkali or alkaline earth salt per gm atom of ruthenium or osmium present in the reaction mixture. The preferred ratios are Ca 5–15 (see Table II).

The following are typical combinations of ruthenium-co-catalyst combinations useful in the inventive process: ruthenium chloride-cesium acetate, ruthenium(IV) oxide-cesium acetate, ruthenium chloride-cesium trifluoroacetate, ruthenium chloride-sodium acetate, ruthenium chloride-cesium proprionate, triruthenium dodecacarbonylcesium acetate, ruthenium oxide-cesium fluoride. Their effectiveness is illustrated in Examples XVIII–XXVIII.

Salts of quaternary ammonium and phosphonium cations are also effective as co-catalysts in the process of this invention. Suitable quaternary phosphonium salts are those which are substantially inert under the CO-hydrogeation conditions and which have the formula:

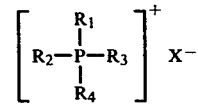

where $R_1$, $R_2$, $R_3$ and $R_4$ are ogranic radicals bonded to the phoshorous atom by a saturated aliphatic carbon atom, and X is an anionic species, preferably of a carboxylic acid, defined below. The organic radicals useful in this instance include those having 1 to 20 carbon atoms in a branched or linear alkyl chain; they include the methyl, ethyl, n-butyl, iso-butyl, octyl, 2-ethylhexyl and dodecyl radicals. Tetramethylphosphonium acetate and tetrabutylphosphonium acetate are typical examples presently in commercial production. The corresponding quaternary phosphonium and ammonium hydroxides, nitrates and halides, such as the corresponding chlorides, bromides and iodides, are also satisfactory in this instance, as are quaternary ammonium salts of carboxylic acids such as tetra-n-butylammonium acetate, and tetra-n-octylammonium propionate as well as the corresponding iminium salts such as bis(triphenylphosphine)iminium acetate. Examples XVII, XVIII, XXXII and XXXIII provide evidence of the effectiveness of the ruthenium chloride-tetrabutylphosphonium acetate couple.

Similar catalyst combinations, containing osmium rather than ruthenium as the transition-metal component, are also suitable for the desired synthesis of alkanol and polyhydric alcohol esters from synthesis gas.

Having described the inventive process in general terms, the following examples are submitted to supply specific and illustrative embodiments. Examples I–XIII and XVI illustrate the basic invention improved upon here.

EXAMPLE I to a degassed sample of acetic acid (50 ml) contained in a 300 ml glass-lined reactor equipped for pressurizing, heating and means of agitation is added, under a nitrogen environment, 0.40 gm of ruthenium acetylacetonate (1.0 mmole). The reactor is sealed, flushed with $CO/H_2$ and pressured to 2700 psi with synthesis gas (184 atm. 1:1, $CO/H_2$). The mixture is then heated to 220° C., with agitation, for 18 hr, and then allowed to cool. Gas uptake is 400 psi. Excess gas is sampled and vented, the yellow-red liquid product, analyzed by glc, shows the presence of: 1
  1.9% methyl acetate
  0.3% ethyl acetate
  1.4% ethylene glycol diacetate. Yellow, crystalline triruthenium dodecacarbonyl slowly precipitates from this product solution upon standing and upon exposure to air.
The vented off-gas typically has the composition:
  47% hydrogen
  48% carbon monoxide
  1.3% carbon dioxide
  2.2% methane.

EXAMPLE II

In the preparation, CO-hydrogenation is carried out as described in Example I, except that the charge mixture consists of 0.426 gm of triruthenium dodecacarbonyl (0.66) solubilized in 50 ml of acetic acid. Analysis of the product liquid by glc shows the presence of:
  4.2% methyl acetate
  0.5% ethyl acetate
  0.4% ethylene glycol diacetate.

EXAMPLE III

In this preparation, CO-hydrogenation is carried out as described in Example I except that the charge mixture consists of 0.71 gm of tricarbonylbis (triphenylphosphine)-ruthenium (1.0 mmole) in 50 ml of glacial acetic acid. Analysis of the product liquid shows:
  3.4 wt. % methyl acetate
  0.8 wt. % ethyl acetate
  0.2 wt. % ethylene glycol diacetate.

EXAMPLE IV

In this preparation, CO-hydrogenation is carried out as described in Example I, except that the charge mixture consists of 0.722 gm of ruthenium(III) hexafluoroacetylacetonate (1 mmole) in 50 ml of acetic acid. Analysis of the product liquid shows:
  5.7% methyl acetate
  0.2% ethyl acetate
  0.26% ethylene glycol diacetate.

EXAMPLE V

In this preparation, CO-hydrogenation is carried out as described in Example I, except that the charge mixture consists of 0.40 gm of ruthenium(II) acetylacetonate (1 mmole), 0.40 gm of tri-n-butylphosphine, and 50 ml of acetic acid. Analysis of the product liquid shows the presence of significant quantities of methyl acetate, ethyl acetate and ethylene glycol diacetate.

EXAMPLE VI

In this preparation, CO-hydrogenation is carried out as described in Example I, except that the charge mixture consists of 0.598 gm of triosmium dodecacarbonyl (0.66 mmole) solubilized in 50 ml of acetic acid. Analysis of the product liquid by glc shows the presence of methyl acetate and ethylene glycol diacetate.

TABLE I

| Example | Operating Temp (°C.) | Maximum Pressure (psi) | Conc(wt %) In Liquid Product | | | |
|---|---|---|---|---|---|---|
| | | | $H_2O$ | MeOAc | EtOAc | $(CH_2OAc)_2$ |
| 7 | 180 | 6900 | 0.7 | 0.7 | 0.1 | 0.1 |
| 8 | 220 | 1300 | 0.2 | 0.7 | 0.5 | 0.1 |
| 9 | 220 | 2375 | 1.0 | 3.4 | 0.7 | 0.5 |
| 10 | 220 | 4350 | 2.5 | 3.5 | 0.8 | 0.4 |
| 11 | 220 | 6800 | 2.0 | 15.6 | 0.8 | 1.0 |
| 12 | 260 | 7350 | 5.1 | 47.7 | 2.9 | 0.8 |

EXAMPLES VII–XII

In these examples, using the techniques and procedures of Example I, the effect of varying the operating temperature and pressure upon the yield and distribution of acetic ester products has been examined. The standard catalyst here is ruthenium(III) acetylacetonate (1-2 mmole) solubilized in glacial acetic acid. The results are summarized in Table I. It is evident from the data that methyl, ethyl and ethylene glycol acetates may each be generated via CO hydrogenation with the solubilized ruthenium catalyst at least over the operating temperature, pressure ranges of:
  180–260° C.
  1300–7350 psi.

EXAMPLE XIII

Following the procedure of Example I, 0.80 gm of ruthenium acetylacetonate (2.0 mmole) is added to a degassed sample of acetic acid (50 ml) set in the 300 ml glass-lined reactor. The reactor is sealed, flushed with $CO/H_2$ and pressured to 4000 psi with 1:1 synthesis gas. The mixture is then heated to 220° C. with agitation, for 18 hrs, and allowed to cool. Gas uptake is 1000 psi. Excess gas is vented and a small (1 ml) liquid sample recovered for analysis. Glc shows the presence of:
  12.3% methyl acetate
  1.0% ehtylene glycol diacetate
  0.5% ethyl acetate
The remainder of the product liquid is recycled to the 300 ml reactor, repressured with 1:1 synthesis gas, and CO-hydrogenation effected as described above. The final product after repeated cycling shows the following composition:
  44.9% methyl acetate
  2.2% ethylene glycol diacetate
  1.4% ethyl acetate
together with unreacted acetic acid and an aqueous by-product. The methyl acetate, ehtyl acetate and ethylene glycol diacetate are recovered as overhead fractions via distillation under reduced pressure (0.1-10mm Hg). A bottoms fractions (2 gm) plus crystallized triruthenium dodecacarbonyl (0.2 gm) are recycled to the reactor with fresh acetic acid (50 ml), and conversion of $CO/H_2$ to acetate esters is carried out as described above. Recovered, clear, yellow liquid product (46 ml) shows the presence of:
- 11.6% methyl acetate
- 2.2% ethylene glycol diacetate
- 0.5% ethyl acetate.

The following examples show that seeming equivalent catalysts, cobalt and rhodium are relatively ineffective for use in the process here.

EXAMPLE XIV

In this preparation, CO-hydrogenation is carried out as described in Example 22, except that the charge mixture consists of 0.80 gm of rhodium(III) acetylacetonate (2.0 mmole) and 50 ml of acetic acid. Analysis of the product liquid by glc shows the presence of:
- 0.5% methyl acetate
- 1.2% ethyl acetate
- 0.1% glycol diacetate.

EXAMPLE XV

In this preparation, CO-hydrogenation is carried out as described in Example 22, except that the charge mixture consists of 0.34 gm of dicobalt octacarbonyl (1 mmole) and 50 ml of acetic acid. Analysis of the product liquid (49 ml) by glc shows the presence of:
- 0.7% methyl acetate
- 2.7% ethyl acetate
- 0.1% glycol diacetate.

EXAMPLE XVI

Following the procedure of Example I, 0.40 gm of ruthenium(III) acetylacetonate (1.0 mmole) and 50 ml of trifluoroacetic acid are charged to a glass-lined, 450 ml reactor. The reactor is sealed, flushed with $CO/H_2$, pressured to 4000 psi with $CO/H_2$ (1:1) and heated to 220° C. overnight. Gas uptake is 1400 psi. Upon cooling, the green liquid product, containing suspended solids, is recovered and analyzed by glc. Analysis shows this material to consists of:
- 37% methyl trifluoroacetate
- 2.3% ethyl trifluoroacetate
- 2.2% ethylene glycol di(trifluoroacetate)
- 43.0% unreacted trifluoroacetic acid.

The following Examples XVII-XXXVI illustrate the improvement here.

EXAMPLE XVII

To an 850 ml glass-lined autoclave reactor equipped for pressurizing, heating, cooling and means of agitation is charged 1.04 gm of ruthenium chloride, hydrate (4.0 mmole), 12.7 of tetrabutylphosphonium acetate (40 mmole) and acetic acid (50 gm). Upon stirring, all solids dissolve to give a clear, deep-red solution. The reactor is then sealed, flushed with $CO/H_2$ and pressured to 4000 psi with synthesis gas (272 atm of a 1.1 mixture of hydrogen and carbon monoxide). Over a period of 60-75 minutes, the autoclave is heated, with agitation, to 220° C., and held at temperature overnight. Total gas uptake is 1800 psi. After cooling, the excess gases are sampled and vented, and the deep-red liquid product (58 ml) removed for analysis. There is no solid product fraction.

Analyses of this liquid fraction by gas-liquid phase chromatography (glc) shows the presence of:
- 63.9 wt. % methyl acetate
- 6.28 wt. % ethylene glycol diacetate
- 5.9 wt. % ethyl acetate
- 19.7 wt. % unreacted acetic acid

EXAMPLE XVIII

To a 300 ml glass-lined autoclave equipped for pressurizing, heating and means of agitation is charged 0.52 gm of ruthenium chloride, hydrate (2.0 mmole), 19.08 gm of tetrabutylphosphonium acetate (60 mmole) and acetic acid (25 gm). The mixture is stirred to dissolve solids, the reactor sealed, flushed with $CO/H_2$ and pressured to 4000 psi with synthesis gas (272 atm of 1:1, $CO/H_2$). Over a period of 60-75 minutes, the autoclave is heated, with agitation, to 220° C. and held at temperature overnight. Total gas uptake is 1550 psi. After cooling, the excess gas is vented and the deep-red liquid product (43 ml) removed from the reactor.

Analysis of this liquid fraction by glc shows the presence of:
- 52.3 wt. % methyl acetate
- 6.71 wt. % ethylene glycol diacetate
- 4.2 wt. % ethyl acetate
- 25.4 wt. % unreacted acetic acid.

A similar product distribution is achieved using an equivalent amount of ruthenium(IV) dioxide as the catalyst precursor and tetraethylphosphonium acetate or tetramethylphosphonium acetate as the co-catalyst component.

EXAMPLE XIX

To the autoclave reactor of Example XVII is charged 1.04 gm of ruthenium chloride, hydrate (4.0 mmole), 8.0 gm of cesium acetate and acetic acid (50 gm). Upon stirring, all solids dissolve to give a clear, deep-red solution. The reactor is then sealed, flushed with $CO/H_2$ and pressured to 4000 psi with synthesis gas (272 atm, 1:1, H2/ CO). Over a period of 90 minutes, the autoclave is heated, with agitation, to 220° C. and held at temperature overnight. Total gas uptake is 1000 psi. After cooling, the excess gases are sampled and vented, and the liquid product recovered for analysis. Gas-liquid chromotography shows the presence of:
- 42.0 wt. % methyl acetate
- 5.7 wt. % ethyl acetate
- 3.2 wt. % ethylene glycol diacetate
- 48.4 wt. % unreacted acetic acid.

EXAMPLES XX-XXV

Following the procedure of Example XX, 1.04 gm of ruthenium chloride hydrate (4.0 mmole), acetic acid (50 gm) and various quantities of cesium acetate (0-60 mmole) are charged to the glass-lined reactor. The reactor is sealed, flushed with $CO/H_2$, pressured to 4000 psi with H2/CO(1:1) and heated to 220° C. overnight. Upon cooling, the liquid product is recovered and anaylzed by glc. Table II summarizes the results. The formation of methyl acetate and ehtylene glycol diacetate both appears to be favored by the addition of cesium salt. Both the ruthenium chloride and cesium acetate are readily solubilized in acetic acid, and initial [Cs]/[R] ratios of 5-15 appear to provide the highest yields of glycol diacetate.

TABLE II

| Example | Cesium Salt (mmole) | Cs/Ru Ratio | Conc (wt. %) In Product Liquid | | | |
|---|---|---|---|---|---|---|
| | | | $H_2O$ | MeOAc | EtOAc | $(CH_2OAc)_2$ |
| 20 | 0 | 0 | 6.8 | 19.9 | 23.1 | 0.22 |
| 21 | 4 | 1 | 1.1 | 18.4 | 15.6 | 0.18 |
| 22 | 12 | 3 | 0.4 | 23.0 | 3.8 | 0.86 |
| 23 | 20 | 5 | 0.3 | 38.9 | 4.2 | 2.28 |
| 24 | 40 | 10 | 0.4 | 42.0 | 5.7 | 3.2 |
| 25 | 60 | 15 | 0.5 | 33.1 | 5.6 | 2.66 |

EXAMPLE XXVI

To a 450 glass-lined autoclave reactor equipped for pressurizing, heating, cooling and means of agitation is charged 0.383 gm of ruthenium oxide, hydrate (2.0 mmole), 4.0 gm of cesium acetate and glacial acetic acid (25 gm). The reactor is then sealed, flushed with $CO/H_2$ and pressured to 4000 psi with synthesis gas (272 atm of 1:1, $CO/H_2$). Over a period of 90 minutes, the clave is heated, with agitation, to 220° C., and held at temperature overnight. Total gas uptake is 800 psi. After cooling, the excess gases are sampled and vented, and the brown liquid product (28 gm) containing suspended solids is removed for analysis. The liquid fraction shows the presence of:
- 7.3 wt. % methyl acetate
- 2.59 wt. % ethylene glycol diacetate
- 1.8 wt. % ethyl acetate The vented off-gases typically have the composition:
- 44% hydrogen
- 39% carbon monoxide
- 11% carbon dioxide
- 3.3% methane

EXAMPLE XXVII

Following the procedures of Example XIX, 1.04 gm of ruthenium chloride, hydrate (4.0 mmmole), 3.28 gm of sodium acetate (40 mmole) and 50 gm of acetic acid are charged to a glass-lined reactor. The reactor is flushed with $CO/H_2$, pressured to 4000 psi with $CO/H_2$ (1:1) and heated to 220° C. overnight, gas uptake is 800 psi. Upon cooling, the liquid product is recovered and analyzed by glc. Data are as follows:
- 27.8 wt. % methyl acetate
- 1.8 wt. % ethyl acetate
- 1.67 wt. % ethylene glycol diacetate

EXAMPLE XXVIII

Following the procedures of Example XIX, 1.04 gm of ruthenium chloride hydrate (4.0 mmole), 2.1 gm of cesium propionate (10 mmole) and 25 ml of propionic acid are charged to a glass-lined, 450 ml reactor. The reactor is sealed, flushed with $CO/H_2$, pressured to 4000 psi with $CO/H_2$ (1:1) and heated to 220° C. overnight. When cooling, the yellow liquid product is recovered and analyzed by glc as follows:
- 28.1% methyl propionate
- 1.30% ethylene glycol dipropionate
- 0.3% ethyl propionate
- 64.9% unreacted propionic acid The residual off-gas consists primarily of unreacted carbon monoxide and hydrogen, viz:
- 47% hydrogen
- 43% carbon monoxide
- 7.2% carbon dioxide A similar product distribution is achieved using the equivalent amount of barium propionate as co-catalyst instead of cesium propionate.

EXAMPLE XXIX

Following the procedure of Example XXVI, 0.763 gm of ruthenium oxide, hydrate (4.0 mmole), 12.0 gm of bis(triphenylphosphine)iminium acetate and 50 gm of acetic acid are charged to the glass-lined reactor. The reactor is flushed with $CO/H_2$, pressured to 4000 psi with $CO/H_2$ (1:1) and heated to 220° C. overnight. Upon cooling, the liquid product is recovered and analyzed by glc. Analysis shows the presence of:
- 26.7 wt. % of methyl acetate
- 9.5 wt. % of ethyl acetate
- 7.6 wt. % of water
- 1.39 wt. % of glycol diacetate Similar methyl, ethyl and glycol acetate yield distributions are achieved using an equivalent quantity of bis(triphenylphosphine)iminium nitrate, tetramethylammonium acetate and/or tetrapropylammonium acetate as the cocatalyst component, instead of bis(triphenylphosphine)iminium acetate.

EXAMPLE XXX

Here the procedures, ruthenium catalyst and solvent of Example XVII are employed, but the reactor is pressured to 4000 psi with a 2:1 mixture of hydrogen and carbon monoxide. After heating to 220° C., with agitation, the cooled liquid product shows the presence of:
- 29.4 wt. % methyl acetate
- 11.4 wt. % ethyl acetate
- 0.9 wt. % ethylene glycol diacetate
- 5.4 wt. % water
- 48.3 wt. % unreacted acetic acid.

EXAMPLE XXXI

Again the procedures, ruthenium catalyst and solvent of Example XVII are employed, but the reactor is pressured to 4000 psi with a 1:2 mixture of hydrogen and carbon monoxide. After having to 220° C., with agitation, the cooled liquid shows the presence of:
- 33.6 wt. % methyl acetate
- 11.8 wt. % ethyl acetate
- 2.60 wt. % ethylene glycol diacetate
- 47.4 wt. % unreacted acetic acid.

EXAMPLE XXXII

To an 850 ml glass-lined autoclave equipped with pressurizing, heating, cooling and means of agitation is charged 1.04 gm of ruthenium chloride hydrate (4.0 mmole), 12.7 gm of tetrabutylphosphonium acetate and glacial acetic acid (50 gm). The reactor is then sealed, flushed with $CO/H_2$ and pressured to 2000 psi with synthesis gas (136 atm of 1:1, $CO/H_2$). Heat is applied to the reactor and contents, the mixture agitated, and when the temperature reaches 220° C., the pressure is raised to 6300 psi (429 atm) with 1:1 synthesis gas. The temperature is maintained at 220° C. overnight, the pressure is held in the range 6000–6300 psi by continuous addition of more syngas. Upon cooling, the excess gases are sampled and vented, and the deep-red liquid product (62 gm) is removed for analysis. There is no solid product. The liquid fraction, analyzed by glc, shows the presence of:
- 61.9 wt. % methyl acetate
- 8.2 wt. % ethyl acetate
- 5.61 wt. % ethylene glycol diacetate 18.3 wt. % unreacted acetic acid.

EXAMPLE XXXIII

Following the procedure of Example XXXII, 1.04 gm of ruthenium chloride, hydrate (4.0 mmole), 50 gm of glacial acetic acid and 10.72 gm of tetrabutylphosphonium acetate, freshly prepared from tri-n-butylphosphine and n-butyl acetate, are charged to an 850 ml glass-lined autoclave. The reactor is sealed, flushed with $CO/H_2$ and pressured to 2000 psi with synthesis gas (136 atm of 1:1, $CO/H_2$). Heat is applied to the reactor and contents, the mixture agitated, and when the temperature reaches 220° C., the pressure is raised to 6300 psi (429 atm) with 1:1 synthesis gas. The temperature is maintained at 220° C. overnight, the pressure is held in the range 6000–6300 psi by continuous addition of more syngas. Upon cooling, the excess gases are sampled and vented, and the deep-red liquid product (62 gm) is recovered for analysis. There is no solid product. The liquid fraction, analyzed by glc, shows the presence of:

66.8 wt. % methyl acetate
7.2 wt. % ethyl acetate
6.11 wt. % ethylene glycol diacetate
2.07 wt. % ethylene glycol monocetate.

EXAMPLE XXXIV

Following the procedure of Example XXX, 1.04 gm of ruthenium chloride hydrate (4.0 mmole), acetic acid (50 gm), together with cesium acetate (40 mmole) and triethylphosphate (12 mmole), are charged to the glass-lined reactor. The reactor is sealed, flushed with $CO/H_2$ pressured to 4000 psi with $CO/H_2$ (1:1) and heated to 220° C. overnight. Upon cooling, the deep-red liquid product is recovered and analyzed by glc as follows:

22.1 wt % methyl acetate
17.6 wt. % ethyl acetate
2.86 wt. % ethylene glycol diacetate
54.5 wt. % unreacted acetic acid.

EXAMPLE XXXV

Following the procedure of Example XIX, 1.04 gm of ruthenium chloride hydrate (4.0 mmole), acetic acid (50 gm), together with cesium acetate (40 mmole) and triphenylphosphite (12 mmole) are charged to the glass-lined reactor. The reactor is sealed, flushed with $CO/H_2$, pressured to 4000 psi with $CO/H_2$ (1:1) and heated to 220° C. overnight. Upon cooling, the deep-red liquid product (52 ml) is recovered and analyzed by glc as follows:

26.6 wt. % methyl acetate
16.5 wt. % ethyl acetate
2.55 wt. % ethylene glycol diacetate
50.8 wt. % unreacted glacial acetic acid.

EXAMPLE XXXVI

Following the procedure of Example XIX, 1.04 gm of ruthenium chloride, hydrate (4.0 mmole), acetic acid (50 gm), together with cesium acetate (40 mmole) and triethylamine (4 mmole), are charged to the glass-lined reactor. The reactor is sealed, flushed with $CO/H_2$ (1:1), pressured to 4000 psi with $CO/H_2$ (1:1) and heated to 220° C. overnight. Upon cooling, the deep-red liquid product is recovered and analyzed by glc as follows:

38.1 wt. % methyl acetate
8.1 wt. % ethyl acetate
2.69 wt. % ethylene glycol diacetate
47.6 wt. % unreacted acetic acid.

As the examples and preceeding discussion have documented, numerous advantages accrue from the practice of this invention both in its compositional and process aspects. In particular a process is disclosed that is which are useful for the one-step conversion of synthesis gas to alkanol and polyhydric alcohol ester derivatives. More specifically, it is disclosed that the activity of the ruthenium and osmium catalysts is significantly improved through the addition of certain classes of co-catalyst species, and particularly by the presence of large cationic species. In the presence of said co-catalyst combinations multiple syntheses of desired product has been demonstrated.

Finally, the invention is advantageous in that numerous substitutions, modifications and changes can be made without departing from the inventive concept. However, the scope of the subject invention may best be understood by examining the claims, which follow, read in conjunction with the preceeding specification.

I claim:
1. In a process for the synthesis of vicinal glycol esters from mixtures of carbon monoxide and hydrogen which comprises the following steps:
 (a) Contacting said mixtures of carbon monoxide and hydroigen with a liquid medium containing one or more aliphatic carboxylic acids and a catalyst containing a ruthenium or osmium transition-metal or mixtures thereof,
 (b) Heating said reaction mixture to a temperature of between about 100° C. and 350° C., at superatmospheric pressures of 500 psi or greater with sufficient carbon monoxide and hydrogen to satisfy the stoichiometry of the desired ester syntheses, until substantial formation of the desired esters of the vicinal glycols has been achieved,
 (c) The improvement which comprises also contacting said mixture with a co-catalyst species selected from the group consisting of alkali metal salts, alkaline earth metal salts, quaternary ammonium salts, iminium salts and quaternary aliphatic phosphonium salts.

2. The method of claim 1 wherein said vicinal glycol esters are isolated.

3. The process of claim 1 wherein the ruthenium-containing catalyst is a ruthenium oxide.

4. The process of claim 3 wherein the ruthenium oxide is selected from the group consisting of ruthenium(IV) dioxide, ruthenium(IV)dioxided hydrate and ruthenium(VIII) tetraoxide.

5. The process of claim 1 wherein the ruthenium-containing catalyst is the salt of a carboxylic acid.

6. The process of claim 5 wherein the ruthenium salt is selected from the group consisting of ruthenium acetate, ruthenium propionate, ruthenium butyrate, ruthenium trifluoroacetate, ruthenium acetylacetonate and ruthenium hexafluoroacetylacetonate.

7. The process of claim 1 wherein the ruthenium-containing catalyst is the salt of a mineral acid.

8. The process of claim 7 wherein the ruthenium salt is selected from the group consisting of ruthenium chloride hydrate, ruthenium bromide and anhydrous ruthenium chloride.

9. The process of claim 1 wherein the ruthenium-containing catalyst also contains one or more Group VB tertiary donor ligands.

10. The process of claim 9 wherein the Group VB tertiary donor ligands are selected from the group consisting of triphenylphosphine, tri-n-butylphosphine, triphenylphosphite, triethylphosphite, trimethylphosphine, triphenylarsine, trimethylamine, triethylamine, tripropylamine, and tri-n-octylamine.

11. The process of claim 1 wherein the carboxylic acid co-reactant is an aliphatic carboxylic acid of 1 to 12 carbon atoms.

12. The process of claim 11 wherein the aliphatic carboxylic acid is selected from the group consisting of acetic acid, propionic acid and butyric acid.

13. The process of claim 11 where the carboxylic acid co-reactant is a substituted aliphatic carboxylic acid selected from the group consisting of trifluoroacetic, dichloroacetic and monofluoroacetic acids.

14. The process of claim 1 wherein the ruthenium catalyst precursor is residual catalyst from previous syntheses of alcohol and vicinal glycol esters from $CO/H_2$ mixtures.

15. The process of claim 1 wherein the alkali metal co-catalyst is an alkali metal salt of a carboxylic acid.

16. The process of claim 15 wherein the alkali metal salt is selected from the group consisting of cesium acetate, cesium propionate, cesium butyrate, sodium acetate and cesium trifluoroacetate.

17. The process of claim 1 wherein the quaternary ammonium co-catalyst is a quaternary ammonium salt of a carboxylic acid.

18. The process of claim 17 wherein the quaternary ammonium salt is selected from the group consisting of tetramethylammonium acetate and tetrapropylammonium acetate.

19. The process of claim 1 wherein the iminium salt co-catalyst is selected from the group consisting of bis(triphenylphosphine)iminium acetate and bis(triphenylphosphine)iminium nitrate.

20. The process of claim 1 wherein the alkali metal co-catalyst is present in about 5 to about 15 moles per gram atom of ruthenium.

21. The process of claim 1 wherein the quaternary phosphonium co-catalyst is a quaternary phosphonium salt of a carboxylic acid.

22. The process of claim 21 wherein the quaternary phosphonium salt is selected from the group consisting of tetramethylphosphonium acetate and tetrabutylphosphonium acetate.

23. A process for the synthesis of ethylene glycol diacetate from mixtures of carbon monoxide and hydrogen which comprises the following steps:
(a) Contacting said mixtures of carbon monoxide and hydrogen with acetic acid and a catalyst containing ruthenium or osmium transition-metal or mixtures thereof,
(b) Heating said reaction mixture to a temperature of between about 100° C. and 350° C., at superatmospheric pressures of 500 psi or greater with sufficient carbon monoxide and hydrogen to satisfy the stoichiometry of the desired ester synthesis until substantial formation of the desired ethylene glycol diacetate has been achieved along with methyl acetate and ethyl acetate co-products;
(c) The improvement which comprises also contacting said mixture with a co-catalyst species selected from the group consisting of alkali metal salts, alkaline earth metal salts, quaternary ammonium salts, iminium salts and quaternary aliphatic phosphonium salts.

24. The process of claim 23 wherein said ethylene glycol diacetate is isolated from said co-products.

* * * * *